(12) United States Patent
Weiss et al.

(10) Patent No.: US 8,900,321 B2
(45) Date of Patent: Dec. 2, 2014

(54) IMPLANT ANCHORING DEVICE

(75) Inventors: Joshua B. Weiss, Landing, NJ (US);
Todd Sekundiak, Omaha, NE (US);
Mobarakh Mohammed, Bronx, NY
(US); John Chernosky, Brick, NJ (US);
Natalia Fridshtand, Ringwood, NJ (US)

(73) Assignee: Zimmer, Inc., Warsaw, IN (US)

( * ) Notice: Subject to any disclaimer, the term of this patent is extended or adjusted under 35 U.S.C. 154(b) by 609 days.

(21) Appl. No.: 11/688,048

(22) Filed: Mar. 19, 2007

(65) Prior Publication Data

US 2008/0046091 A1 Feb. 21, 2008

Related U.S. Application Data

(60) Provisional application No. 60/743,570, filed on Mar. 20, 2006.

(51) Int. Cl.
*A61F 2/34* (2006.01)
*A61B 17/86* (2006.01)
(Continued)

(52) U.S. Cl.
CPC ........... *A61B 17/8605* (2013.01); *A61B 17/686* (2013.01); *A61B 17/744* (2013.01); *A61B*
(Continued)

(58) Field of Classification Search
USPC .......... 623/20.15, 22.32, 22.35–22.38, 22.42, 623/22.46
See application file for complete search history.

(56) References Cited

U.S. PATENT DOCUMENTS 3,840,904 A * 10/1974 Tronzo ...................... 623/22.32
3,939,497 A 2/1976 Heimke et al.
(Continued)

FOREIGN PATENT DOCUMENTS

EP 0013863 A1 8/1980
EP 0169978 A1 2/1986
(Continued)

OTHER PUBLICATIONS

High-Porosity Titanium, Stainless Steel, and Superalloy Parts; Martin Bram, Cornelia Stiller, Hans Pater Buchkremer, Detlev Stover, and Hartmut Baur; Advanced Engineering Materials 2000, 2, No. 4; pp. 196-199.*

*Primary Examiner* — Bruce E Snow
*Assistant Examiner* — Melissa Hoban
(74) *Attorney, Agent, or Firm* — Schwegman Lundberg & Woessner, P.A.

(57) ABSTRACT

An anchor for securing an implant within bone. In one embodiment, the anchor is used to aid in securing an acetabular cup within an acetabulum. The anchor may be implanted within an ischial defect of the pelvis, and is attached to an outer surface of the acetabular cup shell. The anchor is made at least in part of, and may be made entirely of, a porous metal material to facilitate the ingrowth of surrounding bone into the anchor for osseointegrating the anchor into the surrounding bone. The anchor may be secured to the acetabular shell by a screw fastener or by cement, for example. The anchor may be secured to the acetabular shell before the anchor and the acetabular shell are together implanted into the acetabulum, or the anchor may be implanted into the ischial defect, followed by seating the acetabular shell in the acetabulum and then securing the acetabular shell to the anchor.

21 Claims, 9 Drawing Sheets

(51) Int. Cl.
  *A61B 17/68* (2006.01)
  *A61B 17/74* (2006.01)
  *A61F 2/08* (2006.01)
  *A61F 2/30* (2006.01)
  *A61F 2/28* (2006.01)
  *A61F 2/38* (2006.01)
  *A61F 2/40* (2006.01)
  *A61F 2/46* (2006.01)

(52) U.S. Cl.
  CPC ... 17/8685 (2013.01); *A61F 2/0811* (2013.01); *A61F 2/30721* (2013.01); *A61F 2/34* (2013.01); *A61B 17/86* (2013.01); *A61F 2/28* (2013.01); *A61F 2/30744* (2013.01); *A61F 2/30767* (2013.01); *A61F 2/38* (2013.01); *A61F 2/3804* (2013.01); *A61F 2/40* (2013.01); *A61F 2/4637* (2013.01); *A61F 2002/0835* (2013.01); *A61F 2002/0858* (2013.01); *A61F 2002/0864* (2013.01); *A61F 2002/0888* (2013.01); *A61F 2002/30006* (2013.01); *A61F 2002/30011* (2013.01); *A61F 2002/3021* (2013.01); *A61F 2002/30433* (2013.01); *A61F 2002/30448* (2013.01); *A61F 2002/30449* (2013.01); *A61F 2002/3056* (2013.01); *A61F 2002/30594* (2013.01); *A61F 2002/30772* (2013.01); *A61F 2002/30787* (2013.01); *A61F 2002/30794* (2013.01); *A61F 2002/30807* (2013.01); *A61F 2002/30827* (2013.01); *A61F 2002/30871* (2013.01); *A61F 2002/30879* (2013.01); *A61F 2002/30896* (2013.01); *A61F 2002/3092* (2013.01); *A61F 2002/30981* (2013.01); *A61F 2002/3401* (2013.01); *A61F 2002/3443* (2013.01); *A61F 2002/4638* (2013.01); *A61F 2220/0041* (2013.01); *A61F 2220/005* (2013.01); *A61F 2230/0067* (2013.01); *A61F 2250/0015* (2013.01); *A61F 2250/0023* (2013.01); *A61F 2250/0074* (2013.01); *A61F 2310/00161* (2013.01); *A61F 2310/00491* (2013.01); *A61F 2310/00544* (2013.01)
  USPC .................. 623/22.35; 623/22.32; 623/22.36; 623/22.37; 623/22.38

(56) References Cited

U.S. PATENT DOCUMENTS

| | | | |
|---|---|---|---|
| 4,563,778 | A | 1/1986 | Roche et al. |
| 4,566,138 | A | 1/1986 | Lewis et al. |
| 4,685,923 | A | 8/1987 | Mathys |
| 4,769,041 | A | 9/1988 | Morscher |
| 4,792,337 | A | 12/1988 | Muller |
| 4,828,565 | A | 5/1989 | Duthoit et al. |
| 4,923,473 | A | 5/1990 | Griss et al. |
| 4,955,917 | A | 9/1990 | Karpf |
| 5,108,446 | A * | 4/1992 | Wagner et al. ............. 623/22.28 |
| 5,211,665 | A * | 5/1993 | Ku ............................ 623/22.38 |
| 5,314,487 | A * | 5/1994 | Schryver et al. ........... 623/22.37 |
| 5,360,452 | A * | 11/1994 | Engelhardt et al. ........ 623/22.37 |
| 5,507,827 | A * | 4/1996 | Grundei et al. ............ 623/22.35 |
| 6,228,121 | B1 * | 5/2001 | Khalili ....................... 623/22.36 |
| 2002/0161369 | A1 * | 10/2002 | Bramlet et al. ................. 606/67 |
| 2004/0088056 | A1 * | 5/2004 | Lewallen ................... 623/22.11 |
| 2004/0093090 | A1 * | 5/2004 | Barbieri et al. .............. 623/22.3 |
| 2006/0241776 | A1 * | 10/2006 | Brown et al. .............. 623/20.16 |
| 2008/0195221 | A1 * | 8/2008 | Howald et al. ............. 623/22.32 |

FOREIGN PATENT DOCUMENTS

| | | |
|---|---|---|
| EP | 0211169 A1 | 2/1987 |
| EP | 0212087 A1 | 3/1987 |
| EP | 0341198 A1 | 11/1989 |
| GB | 1170295 A | 11/1969 |
| GB | 2080118 A | 7/1980 |

* cited by examiner

FIG_4

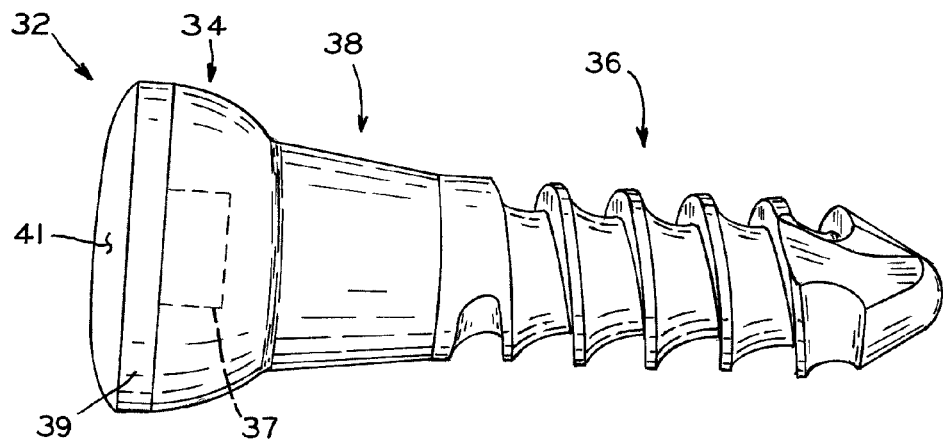
FIG_6
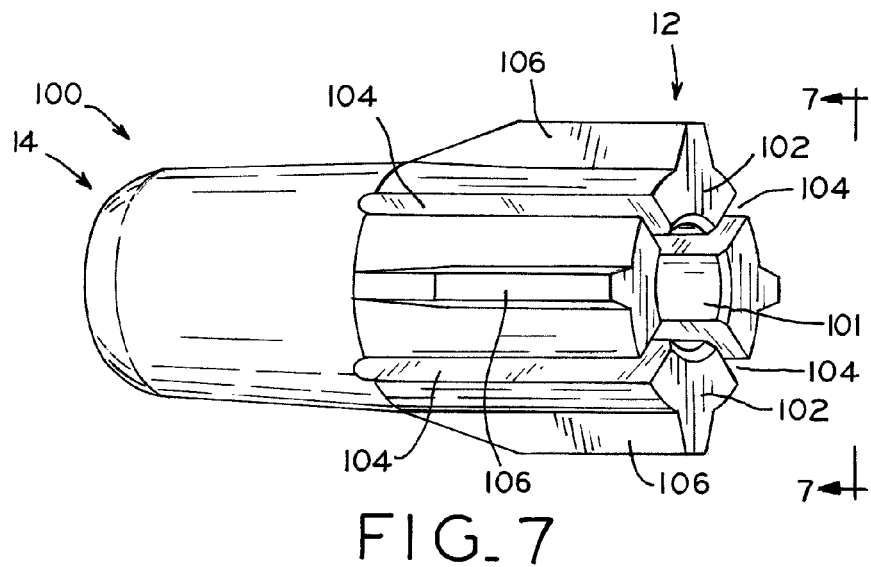
FIG_7
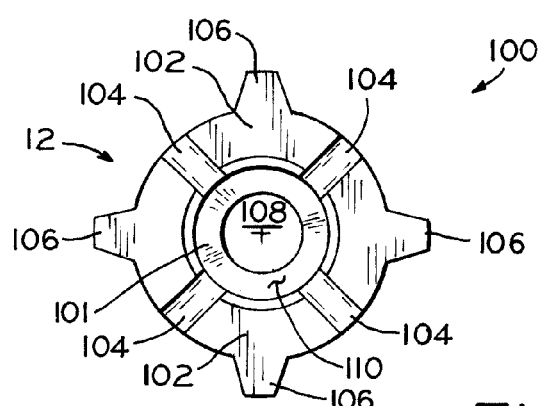
FIG_8

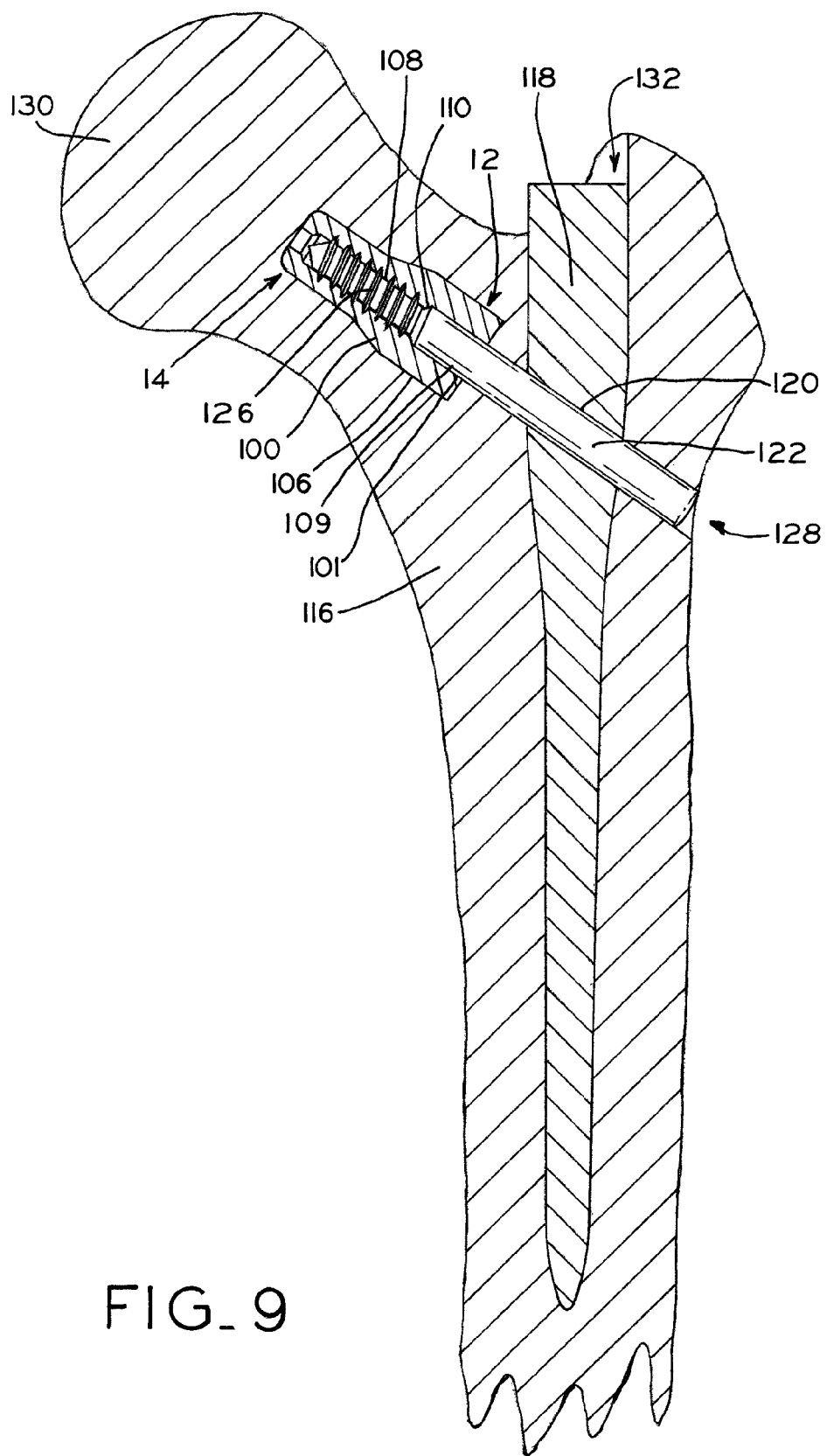
FIG_9

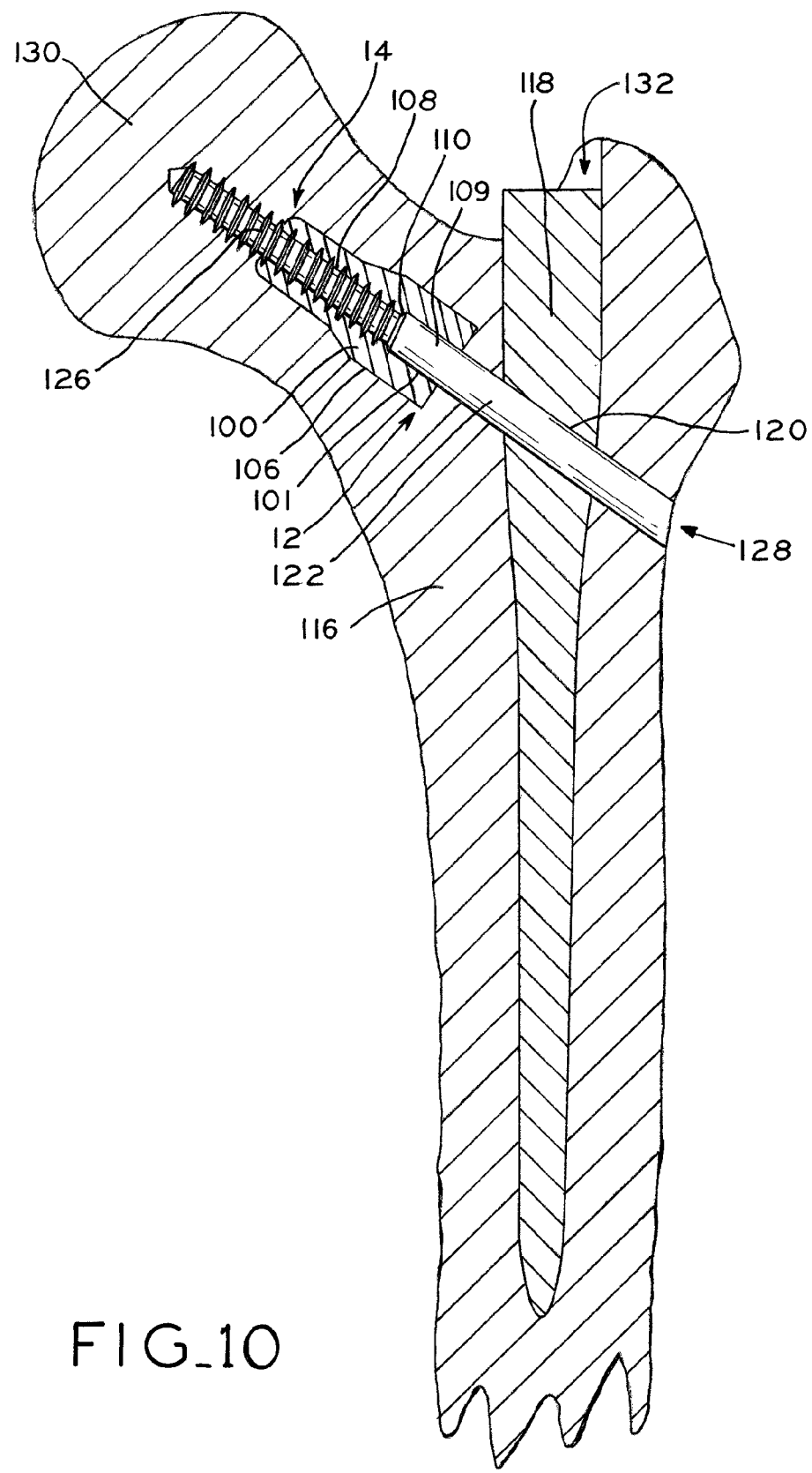
FIG_10

IMPLANT ANCHORING DEVICE

CROSS-REFERENCE TO RELATED APPLICATIONS

This application claims the benefit under Title 35, U.S.C. §119(e) of U.S. Provisional Patent Application Ser. No. 60/743,570, entitled Implant Anchoring Device, filed on Mar. 20, 2006, the disclosure of which is expressly incorporated herein by reference.

BACKGROUND

1. Field of the Invention

The present invention relates to an anchoring device for securing an implant within bone, such as for securing an acetabular cup with an acetabulum during a total hip arthroplasty, for example.

2. Description of the Related Art

Orthopedic implants are commonly used to replace some or all of a patient's joint in order to restore the use of the joint, or to increase the use of the joint, following deterioration due to aging or illness, or injury due to trauma. In a hip replacement, or hip arthroplasty procedure, a femoral component is used to replace a portion of the patient's femur, including the femoral neck and head. The femoral component is typically a hip stem, which includes a stem portion positioned within the prepared femoral canal of the patient's femur and secured via bone cement, or by a press-fit followed by bony ingrowth of the surrounding tissue into a porous coating of the stem portion, for example. The hip stem also includes a neck portion adapted to receive a prosthetic femoral head. The femoral head is received within a prosthetic acetabular component, such as an acetabular cup received within the prepared recess of the patient's acetabulum.

Defects in the bone stock of the ischium of the pelvis may increase the difficulty of anchoring the acetabular component, necessitating the use of bone screws or other anchoring devices to anchor the acetabular component within the acetabulum.

SUMMARY

The present invention provides an anchor for securing an implant within bone. In one embodiment, the anchor is used to aid in securing a primary implant component, such as an acetabular cup, within an acetabulum. The anchor may be implanted within an ischial defect of the pelvis, and is attached to an outer surface of the shell of an acetabular cup. The anchor is made at least in part of, and may be made entirely of, a porous metal material to facilitate the ingrowth of surrounding bone into the anchor for osseointegrating the anchor into the surrounding bone. The anchor may be secured to the acetabular shell by a fastener, such as a screw or bone cement, for example. The anchor may be secured to the acetabular shell before the anchor and the acetabular shell are together implanted into the acetabulum, or the anchor may be implanted into the ischial defect, followed by seating the acetabular shell in the acetabulum and then securing the acetabular shell to the anchor.

In another exemplary embodiment, the anchor may be used in conjunction with another primary implant component, such as an intramedullary nail, within a femur. The anchor may be implanted within the neck of a femur and secured therein via interaction with a fastener. Further, the fastener may be configured for receipt within a bore in the intramedullary nail to secure the anchor thereto. The anchor may be implanted in the femur before the intramedullary nail is implanted into the intramedullary canal of the femur or, alternatively, the intramedullary nail may be implanted into the intramedullary canal of the femur, followed by the implantation of the anchor in the femur.

In one form thereof, the present invention provides an implant assembly, including: a primary implant component formed from a biocompatible material; and an elongate anchor formed from a highly porous biomaterial, the anchor configured for securement to the primary implant component, the anchor having a bore extending at least partially therethrough, the bore dimensioned to receive a fastener therein, whereby receipt of the fastener results in outward expansion of at least a portion of the anchor and facilitates securement of the anchor to the primary implant component.

In another form thereof, the present invention provides an implant assembly, including: a primary implant component formed from a biocompatible material; an anchor formed from a highly porous biomaterial, the anchor having a bore formed therein; and a fastener dimensioned for receipt within the bore formed in the anchor, wherein receipt of the fastener within the bore results in outward expansion of at least a portion of the anchor and facilitates securement of the anchor to the primary implant component.

In yet another form thereof, the present invention provides a method of securing a primary implant component to a bone, including the steps of: inserting an anchor formed from a highly porous biomaterial into the bone, the anchor having a bore formed therein; implanting the primary implant component in the bone; and inserting a fastener into the bore formed in the anchor to outwardly expand at least a portion of the anchor, whereby the outward expansion of the anchor facilitates securement of the anchor to the primary implant component and securement of the primary implant component to the bone.

In yet another form thereof, the present invention provides an implant assembly for providing fixation to a bone, the implant assembly including an anchor formed from a highly porous biomaterial, the anchor having a distal end, a proximal end, and an aperture extending at least partially from the proximal end to the distal end; and a fastener receivable within the aperture of the anchor, wherein receipt of the fastener within the aperture results in outward expansion of the anchor to secure the anchor within the bone.

In yet another form thereof, the present invention provides a method of providing fixation to a bone comprising the steps of inserting an anchor formed from a highly porous biomaterial into the bone, the anchor having a bore formed therein; and inserting a fastener into the bore formed in the anchor to outwardly expand at least a portion of the anchor, whereby the outward expansion of the anchor facilitates securement of the anchor to the bone.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 6 is a radial view of the fastener of FIG. 5;

FIG. 7 is a perspective view of an exemplary anchor in accordance with another embodiment;

FIG. 8 is a proximal end view of the anchor of FIG. 7 taken along line 7-7 of FIG. 7;

FIG. 9 is a cross-sectional view of the anchor of FIG. 7 implanted within a femur and secured to an intramedullary nail by a fastener;

FIG. 10 is a cross-sectional view of another exemplary embodiment of the anchor of FIG. 7 with an exemplary internal bore implanted within a femur and secured to an intramedullary nail via a fastener;

Corresponding reference characters indicate corresponding parts throughout the several views. The exemplifications set out herein illustrate preferred embodiments of the invention and such exemplifications are not to be construed as limiting the scope of the invention in any manner.

DETAILED DESCRIPTION

Figure 1:
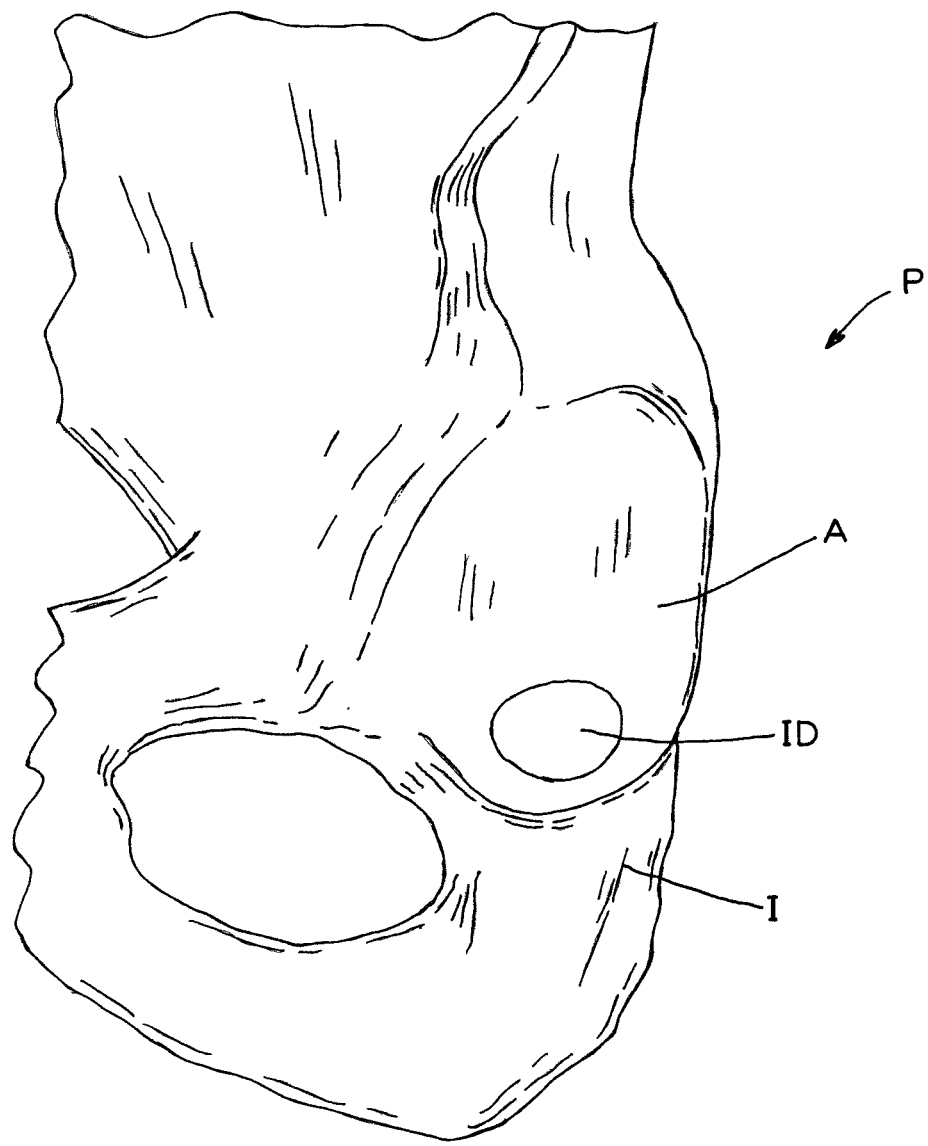
FIG. 1 is a perspective view of a portion of a pelvis, showing the acetabulum and an ischial defect.

Referring to FIG. 1, a portion of pelvis P is shown, including acetabulum A and ischium I. Ischium I includes an ischial defect ID therein, which may be a deterioration of the bone stock of the ischium I due to trauma or disease, for example, and which is shown schematically in FIG. 1 as a hole within ischium I in which an anchor in accordance with the present invention may be implanted.

Figure 2:
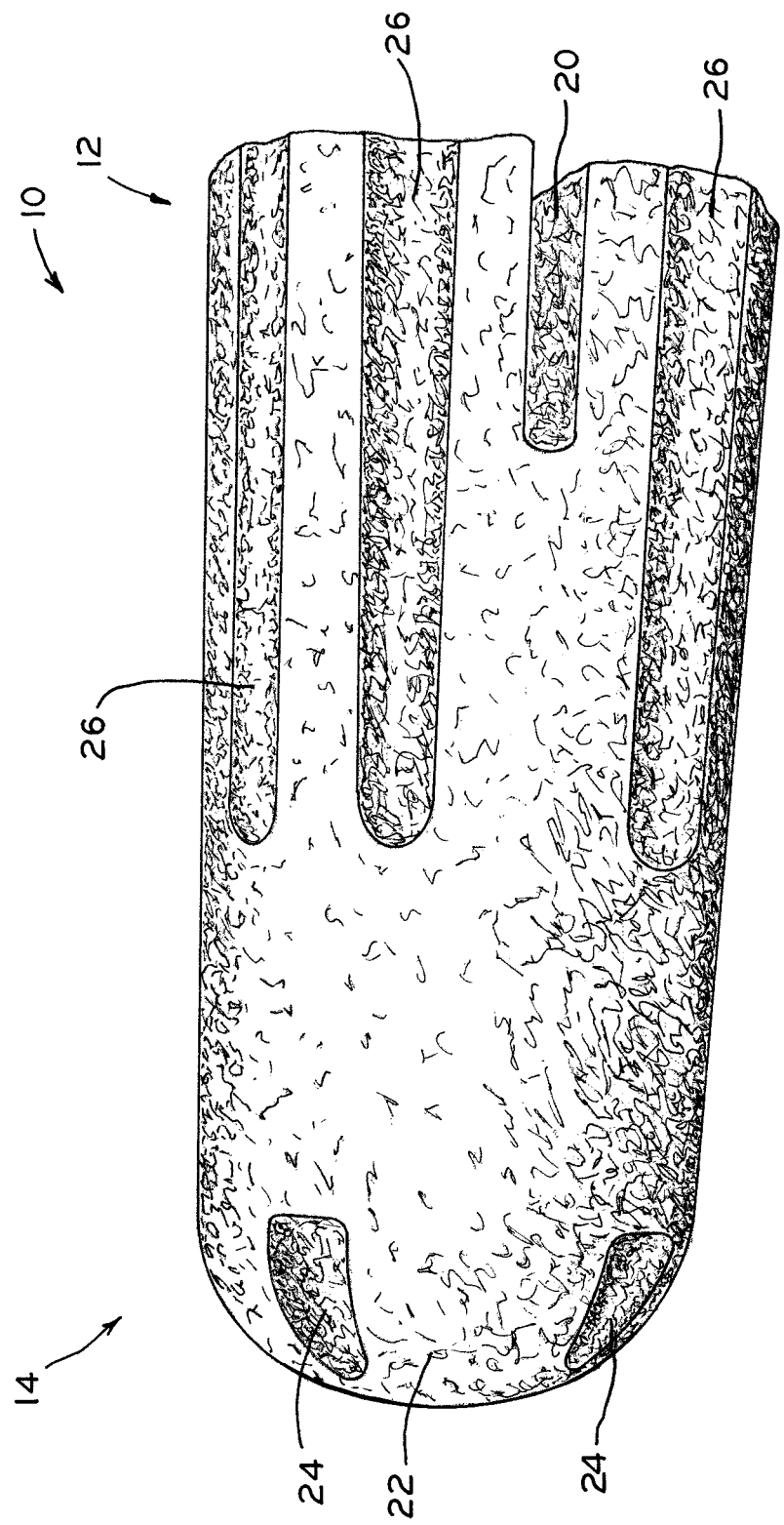
FIG. 2 is a perspective view of an exemplary anchor in accordance with the present invention.
Figure 3:
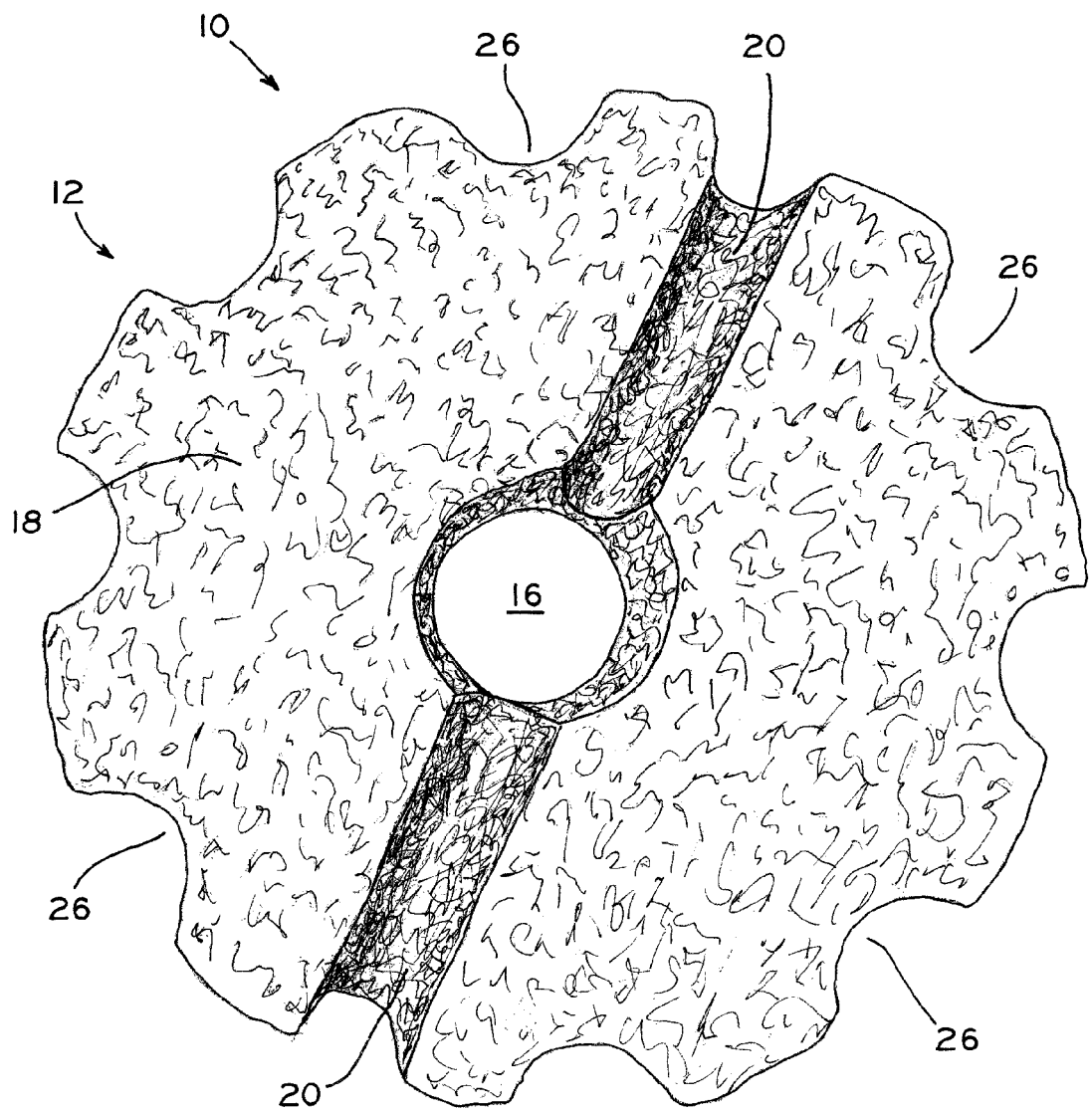
FIG. 3 is a proximal end view of the anchor of FIG. 2.
Figure 4:
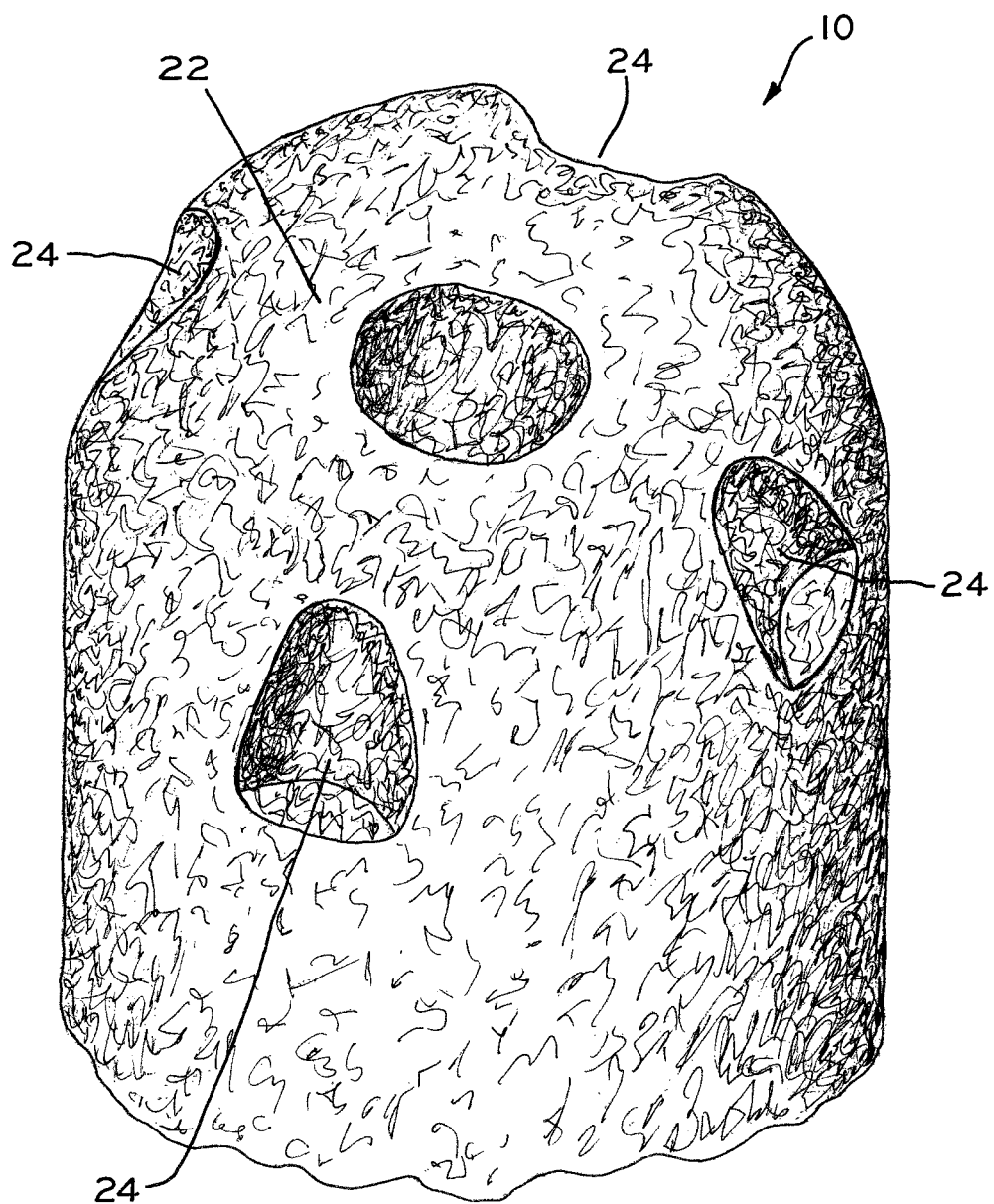
FIG. 4 is a fragmentary perspective view of the distal end of the anchor of FIG. 2.

Referring to FIGS. 2-4, anchor 10 is shown and generally includes a tapered, somewhat bullet-shaped body having proximal end 12, distal end 14, and central cannula or bore 16 extending therethrough. Proximal end 12 includes concave surface 18 for fitting against the convex surface of an acetabular shell, as described below, and groove 20 therein which accommodates radial expansion of anchor 10. In one exemplary embodiment, groove 20 extends from bore 16 to the exterior surface of the body of anchor 10. Distal end 14 includes curved end 22. A plurality of indentations 24 are formed in distal end 14 that may be engaged by a suitable instrument (not shown) to hold anchor 10 while anchor 10 is being secured to an acetabular shell in the manner described below. Anchor 10 may additionally include a plurality of flutes 26 along its outer surface to aid in seating anchor 10 within the ischial defect ID of pelvis P.

Anchor 10 is made at least in part of, and may be made entirely of, a highly porous biomaterial useful as a bone substitute and/or cell and tissue receptive material. A highly porous biomaterial may have a porosity as low as 55, 65, or 75 percent and as high as 80, 85, or 90 percent. An example of such a material is produced using Trabecular Metal™ technology generally available from Zimmer, Inc., of Warsaw, Ind. Trabecular Metal™ is a trademark of Zimmer Technology, Inc. Such a material may be formed from a reticulated vitreous carbon foam substrate which is infiltrated and coated with a biocompatible metal, such as tantalum, etc., by a chemical vapor deposition ("CVD") process in the manner disclosed in detail in U.S. Pat. No. 5,282,861, the disclosure of which is expressly incorporated herein by reference. In addition to tantalum, other metals such as niobium, or alloys of tantalum and niobium with one another or with other metals may also be used.

Generally, the porous tantalum structure includes a large plurality of ligaments defining open spaces therebetween, with each ligament generally including a carbon core covered by a thin film of metal such as tantalum, for example. The open spaces between the ligaments form a matrix of continuous channels having no dead ends, such that growth of cancellous bone through the porous tantalum structure is uninhibited. The porous tantalum may include up to 75%-85% or more void space therein. Thus, porous tantalum is a lightweight, strong porous structure which is substantially uniform and consistent in composition, and closely resembles the structure of natural cancellous bone, thereby providing a matrix into which cancellous bone may grow to provide fixation of anchor 10 in the surrounding bone of ischium I of pelvis P.

The porous tantalum structure may be made in a variety of densities in order to selectively tailor the structure for particular applications. In particular, as discussed in the above-incorporated U.S. Pat. No. 5,282,861, the porous tantalum may be fabricated to virtually any desired porosity and pore size, and can thus be matched with the surrounding natural bone in order to provide an improved matrix for bone ingrowth and mineralization.

In use, during a total hip arthroplasty, for example, referring to FIG. 1, acetabulum A is first reamed in a known manner using a suitable instrument. Exemplary surgical techniques for performing a total hip arthroplasty are described in U.S. Pat. No. 6,676,706, issued Jan. 13, 2004; U.S. Pat. No. 6,860,903, issued Mar. 1, 2005; U.S. Pat. No. 6,953,480, issued Oct. 11, 2005; U.S. Pat. No. 6,991,656, issued Jan. 31, 2006; abandoned U.S. patent application Ser. No. 10/929,736, filed Aug. 30, 2004; currently pending U.S. patent application Ser. No. 10/952,301, filed Sep. 28, 2004; currently pending U.S. patent application Ser. No. 11/235,286, filed Sep. 26, 2005; and currently pending U.S. patent application Ser. No. 11/105,080, filed Apr. 13, 2005, all titled METHOD AND APPARATUS FOR PERFORMING A MINIMALLY INVASIVE TOTAL HIP ARTHROPLASTY and all assigned to the assignee of the present application, the disclosures of which are hereby expressly incorporated herein by reference.

Once acetabulum A has been reamed, ischial defect ID is cleaned and prepared, for example, using a curette. Optionally, the surgeon may ream ischial defect ID. Typically, ischial defect ID is prepared to match the size and shape of anchor 10. Then, a depth gage (not shown) may be used to determine the correct anchor length needed, wherein, during a surgical procedure, a plurality of anchors 10 may be provided having varying sizes and shapes.

Figure 5:
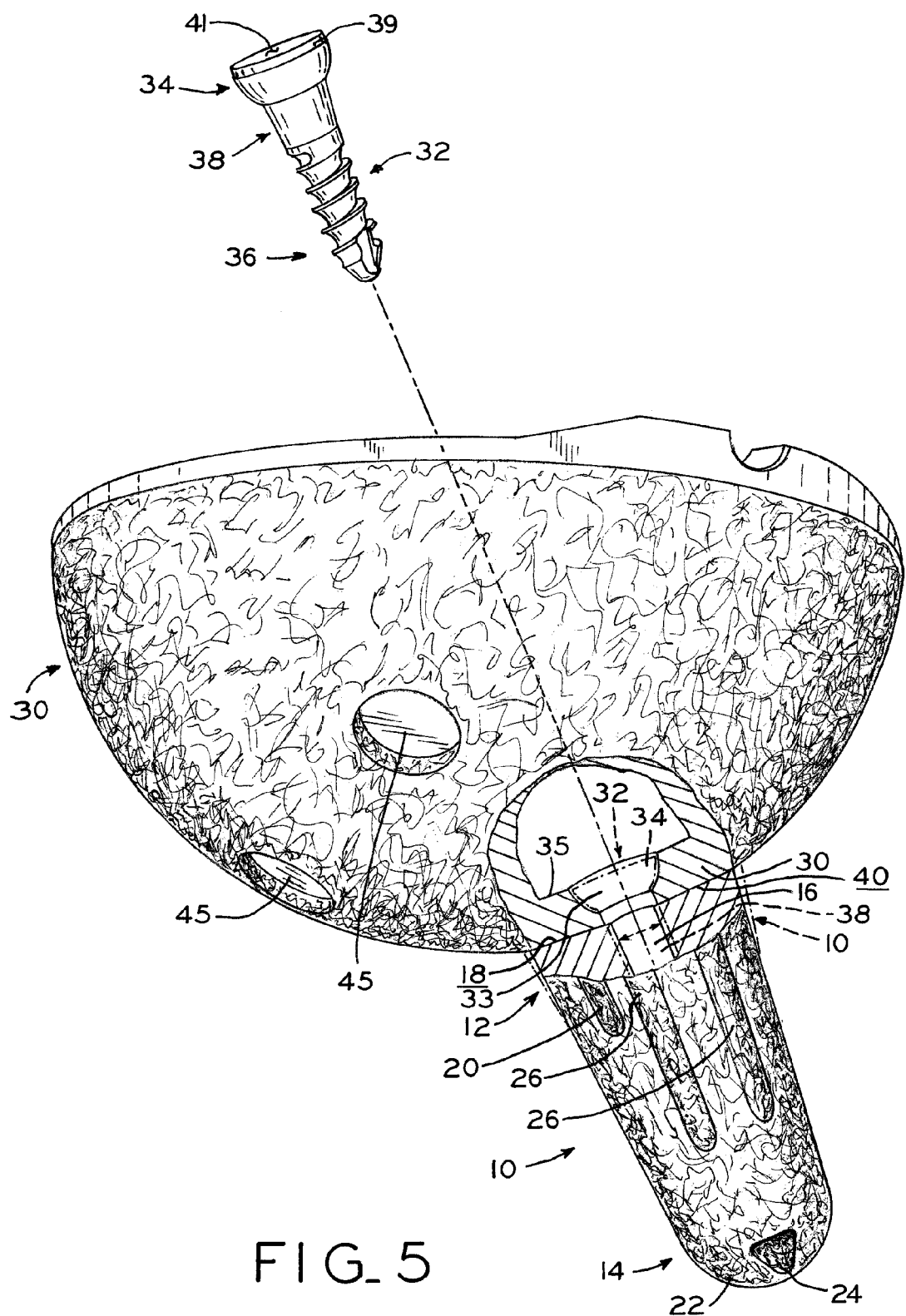
FIG. 5 is a perspective view of a fastener with the anchor of FIGS. 2-4 positioned adjacent to the outer surface of an acetabular shell, the fastener being shown in solid lines apart from the anchor and the acetabular shell, and the fastener being shown in phantom coupled to the anchor and the acetabular shell.

Referring to FIGS. 2-5, in a first embodiment, anchor 10 is attached to acetabular shell 30 before acetabular shell 30 and anchor 10 are implanted. In this embodiment, a suitably sized anchor 10 is then selected and an instrument (not shown) is used to hold anchor 10, by engagement with indentations 24 on distal end 14 of anchor 10, for example, against acetabular shell 30. Thereafter, referring to FIG. 6, cap 39 of screw 32 is removed and a suitable insertion instrument (not shown), such as a screwdriver, is engaged with drive bore 37 of screw 32. Referring to FIG. 5, screw 32 is then inserted from a position apart from the acetabular shell 30 (as shown in solid lines in FIG. 5) to a position through aperture 33 in acetabular shell 30 (as shown in phantom in FIG. 5). As shown in FIG. 6, screw 32 generally includes head 34, threaded portion 36, and tapered section 38 between threaded portion 36 and head 34. The insertion instrument is then used to screw threaded section 36 of screw 32 into central bore 16 of anchor 10 from proximal end 12. As used herein, proximal end 12 denotes the end of anchor 10 closest to head 34 of screw 32 during insertion of screw 32 into anchor 10 and distal end 14 denotes the end of anchor 10 furthest from head 34 of screw 32 during insertion of screw 32 into anchor 10.

As screw 32 is advanced, tapered section 38 of screw 32 engages the smaller diameter interior of central bore 16 causing anchor 10 to radially expand about each side of groove 20 in anchor 10 (as shown in phantom in FIG. 5). Once screw 32 is seated with aperture 33, anchor 10 is secured to acetabular shell 30. Cap 39 is then secured to screw 32 via adhesive or any other known fastener. Additionally, as shown in FIG. 6, cap 39 further includes surface 41. In another exemplary embodiment, cap 39 is absent and drive bore 37 of screw 32 is exposed. In another exemplary embodiment, anchor 10 may be secured to acetabular shell 30 using a biocompatible cement. Additionally, in yet another exemplary embodiment, threaded portion 36 of screw 32 is lengthened to extend from distal end 14 entirely through bore 16. This allows threaded portion 36 to threadingly engage the bone of ischium I of acetabulum A and provide additional fixation thereto.

Referring to FIG. 5, upon securement of anchor 10 to acetabular shell 30, concave surface 18 (FIG. 3) of proximal end 12 of anchor 10 abuts the convex outer surface 40 of acetabular shell 30, which may be made of the same porous metal structure as anchor 10. A torque limiter (not shown) may be used to prevent over tightening of screw 32. Thereafter, referring to FIG. 1, the assembled acetabular shell 30 and anchor 10 are together seated within the acetabulum A, with anchor 10 extending into the ischial defect ID. One or more additional dome screws (not shown) may be threaded through additional apertures 45 in acetabular shell 30 and into the ilium of the pelvis P to provide additional anchorage of acetabular shell 30. Finally, an acetabular liner (not shown), which may be made of ultrahigh molecular weight polyethylene (UHMWPE), for example, is fitted into the acetabular shell 30 to provide an articulating surface against which a femoral component (not shown) may articulate in the prosthetic hip joint.

In another embodiment, anchor 10 may be implanted into the ischial defect ID, followed by seating acetabular shell 30 within the acetabulum A with aperture 33 in the acetabular shell 30 aligned with central bore 16 of anchor 10, followed by inserting screw 32 through aperture 33 in acetabular shell 30 into central bore 16 of anchor 10 to radially expand anchor 10. Thereafter, the procedure is completed in the same manner as described in detail above.

Irrespective of the method used to implant anchor 10 and acetabular shell 30, ischial bone will grow into anchor 10 to osseointegrate anchor 10 within ischium I, thereby providing additional anchoring and fixational stability for acetabular shell 30. Although anchor 10 has been described herein as used with an acetabular cup in the context of a total hip arthroplasty, anchor 10 and/or similar variants thereof may be used to anchor other types of implants within bone in other types of orthopedic procedures, such as knee, shoulder, or elbow arthroplasties, for example.

Figure 11:
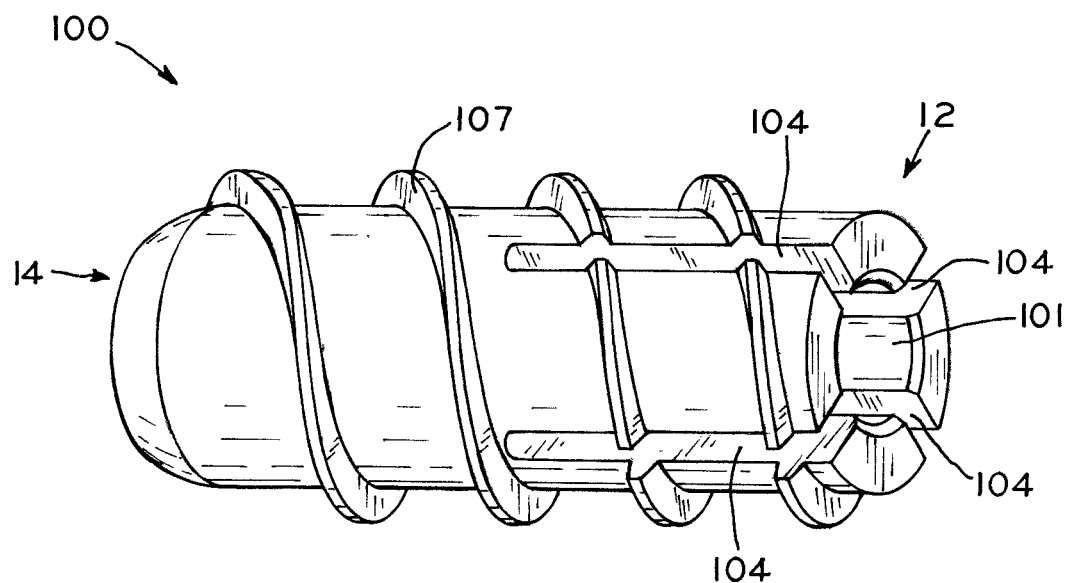
FIG. 11 is a perspective view of an exemplary anchor in accordance with another embodiment.

Additionally, another exemplary embodiment of anchor 10 is depicted in FIGS. 7-9 as anchor 100. Anchor 100 has several features which are identical or substantially identical to corresponding features of anchor 10 and identical reference numerals have been used to identify identical or substantially identical features therebetween. Referring to FIG. 7, anchor 100, includes a somewhat bullet-shaped body having proximal end 12, distal end 14, and central cannula or bore 101 extending therethrough. In contrast to anchor 10, proximal end 12 of anchor 100 includes a substantially planar proximal surface 102. Extending from proximal surface 102 toward distal end 14 are grooves 104. Grooves 104 function in a similar manner as grooves 20 of anchor 10 and facilitate radial expansion of anchor 100. Additionally, extending from the body of anchor 100 are ribs 106, which provide additional fixation of anchor 100 with bone. In another exemplary embodiment, shown in FIG. 11, ribs 106 are replaced by thread 107 extending from the body of anchor 100. Similar to ribs 106, thread 107 also facilitates the fixation of anchor 100 with bone. In another exemplary embodiment, anchor 100 lacks ribs 106. In this embodiment, anchor 100 may have a substantially smooth exterior surface.

As shown in FIG. 9, bore 101 extending through anchor 100 has a first, smaller diameter portion 108 and a second, larger diameter portion 109. Defined between smaller diameter portion 108 and larger diameter portion 109 is shoulder 110. Thus, as a fastener, such as screw 122, is advanced through bore 101, threaded portion 126 of screw 122 will contact shoulder 110 and prevent further advancement of the fastener through bore 101. In this embodiment, threaded portion 126 extends only partially through bore 101. Referring to FIG. 10, another exemplary embodiment is shown in which threaded portion 126 of screw 122 is lengthened to extend from distal end 14 entirely through bore 101. This allows threaded portion 126 to threadingly engage the bone of femur 116 and provide additional fixation thereto. In another exemplary embodiment (not shown), shoulder 110 is absent and bore 101 has the same diameter along the entire length of anchor 100. Alternatively, bore 101 may taper from proximal end 12 to distal end 14, i.e., have a diameter that decreases from proximal end 12 to distal 14.

Anchor 100 may be used in numerous applications where bony ingrowth is desired to facilitate the securement and/or retention of an orthopedic component within a patient's body. Similar to anchor 10, anchor 100 is made at least in part of, and may be made entirely of, a highly porous biomaterial useful as a bone substitute and/or cell and tissue receptive material, such as a material produced using Trabecular Metal™ technology, described in detail above. Referring to FIGS. 8 and 9, anchor 100 is shown in use with intramedullary nail 118. Intramedullary nail 118 extends into the intramedullary canal of femur 116 to facilitate the repair of fractures (not shown) in femur 116, for example. Intramedullary nail 118 includes bore 120 extending therethrough dimensioned to receive a fastener, such as screw 122, therein. Both shaft portion 124 and threaded portion 126 of screw 122 are dimensioned for receipt within at least a portion of bore 101 of anchor 100.

To implant intramedullary nail 118, bore 128 is reamed in femur 116 to extend from a lateral portion of femur 116 in the direction of femoral head 130. Intramedullary bore 132 is then created along the intramedullary canal of femur 116 and dimensioned to receive intramedullary nail 118 therein. Once bores 128, 132 are formed in femur 116, anchor 100 may be inserted and seated within bore 128. Once anchor 100 is positioned within bore 128, intramedullary nail 118 may be inserted within bore 132 and bore 120, which extends through intramedullary nail 118, aligned with bore 128 of femur 116 and bore 101 of anchor 100. In another exemplary embodiment, anchor 100 is sized to pass through bore 120 of intramedullary nail 118. In this embodiment, intramedullary nail 118 may first be implanted as described above and, after intramedullary nail 118 is properly implanted, anchor 100 may be advanced through bores 120, 128 and seated within a medial portion of bore 128.

With bores 128, 120, and 101 aligned as described above, screw 122 is inserted through bores 128, 120, and 101, respectively. As screw 122 is advanced into bore 101 of anchor 100, anchor 100 is expanded radially outward, as described in detail above with respect to anchor 10, to engage the bone of femur 116 defining bore 128. Screw 122 may be advanced until threaded portion 126 engages shoulder 110. In another exemplary embodiment, described above and depicted in FIG. 10, threaded portion 126 of screw 122 is lengthened. In this embodiment, when threaded portion 126 engages shoulder 110, at least a portion of threaded portion 126 extends from distal end 14 of anchor 100. In this embodiment, threaded portion 126 of screw 122 threadingly engages the bone of femur 116 to provide additional fixation of screw 122 and, correspondingly, intramedullary nail 118 to femur 116.

Advantageously, the use of anchor 100 in conjunction with screw 122 provides for additional fixation and retention of screw 122 and intramedullary nail 118 within the body of a patient. Additionally, in the event of revision surgery, anchor 100 provides a point of reattachment for screw 122. Specifically, in the event of a revision of intramedullary nail 118, screw 122 would be removed and an alternate intramedullary nail 118 and screw 122 implanted, all without the removal of anchor 100. Since the previously achieved bone ingrowth and interdigitation of femur 116 with anchor 100 remains intact, screw 122 and intramedullary nail 118 immediately provide a level of fixation otherwise unavailable.

Figure 12:
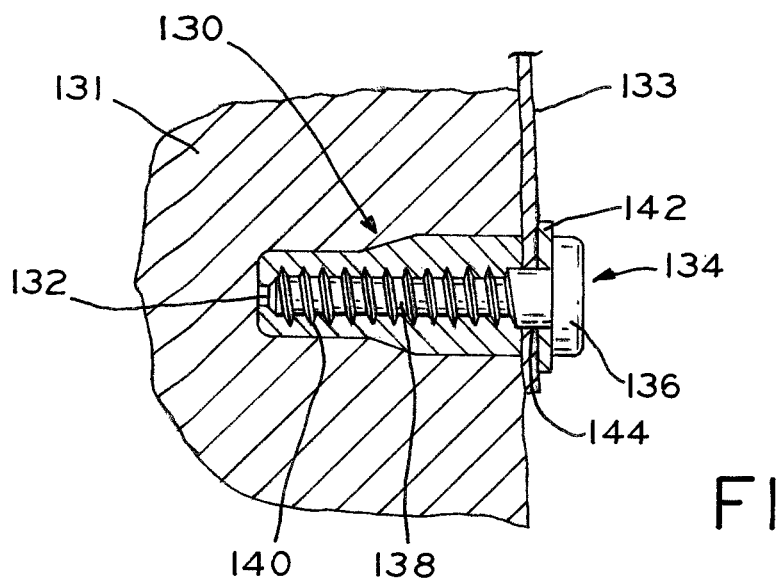
FIG. 12 is a cross-sectional view of an exemplary anchor in accordance with another embodiment implanted within a bone to secure soft tissue thereto.

Referring to FIG. 12, anchor 130 is shown according to another exemplary embodiment. Similar to other embodiments disclosed herein, anchor 130 is made at least in part of, and may be made entirely of, a highly porous biomaterial useful as a bone substitute and/or cell and tissue receptive material, such as a material manufactured using Trabecular Metal™ technology, as discussed in detail above. As shown in FIG. 12, anchor 130 is positioned within bone 131 to facilitate the securement of soft tissue 133 thereto, as described in detail below. While described generically herein as bone 131, bone 131 may be any bone for which it is advantageous to secure soft tissue thereto. For example, bone 131 may be a humerus to which soft tissue is secured during a surgery to repair the rotator cuff. Bore 132 extends through anchor 130 and is dimensioned for receipt of a fastener, such as screw 134, therein and/or therethrough. Screw 134 includes head 136 and shaft 138 having threads 140 extending therefrom. Positioned adjacent head 136 and soft tissue 133 is washer 142. Washer 142 includes aperture 144 dimensioned to receive shaft 138 of screw 134 therethrough and retain washer 142 adjacent head 136 of screw 134. In one exemplary embodiment, washer 142 is made at least in part of, and may be made entirely of, a highly porous biomaterial useful as a bone substitute and/or cell and tissue receptive material, such as a material manufactured using Trabecular Metal™ technology, as discussed in detail above.

To secure soft tissue 133 to bone 131, anchor 130 is initially implanted therein in a similar manner as described above with respect to anchor 10. Washer 142 may then be received on shaft 138 of screw 134. Soft tissue 133 may then be positioned over anchor 130 adjacent bone 131. In one exemplary embodiment, soft tissue 133 may be temporarily secured to bone 131. Once soft tissue 133 is positioned over anchor 130, screw 134 may be advanced through soft tissue 133 and into bore 132 causing expansion of anchor 130 in a similar manner as described in detail above with respect to anchor 10. Additionally, advancement of screw 134 clamps soft tissue 133 between washer 133 and bone 131. Screw 134 may then advanced into and/or through bore 132 to a position sufficient to place a predetermined clamping force on soft tissue 133 that is capable of holding soft tissue 133 in place.

Advantageously, by utilizing anchor 130 to secure soft tissue 133 to bone 131, anchor 130 will facilitate ingrowth of both bone 131 and soft tissue 133 into anchor 130. This ingrowth may provide additional securement of soft tissue 133 to bone 131 that is otherwise unavailable. Further, when washer 142 is also formed at least partially of a highly porous biomaterial, soft tissue 131 may also grow into washer 142 to provide an additional mechanism securing soft tissue 131 in place.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An implant assembly, comprising:
an acetabular shell formed from a biocompatible material, said acetabular shell having a polar axis, a concave inner surface, a convex outer surface, and an aperture extending through said acetabular shell from said concave inner surface to said convex outer surface, said aperture being non-coincident with said polar axis of said acetabular shell; and
an elongate anchor formed entirely from a highly porous biomaterial, said highly porous biomaterial having a porosity of between 55 and 90 percent, said anchor configured for securement to said acetabular shell, said anchor having a bore extending at least partially therethrough, said bore configured to be aligned with said aperture of said acetabular shell so that a fastener can be received through said aperture in said acetabular shell and into said bore of said anchor to cause at least a portion of said anchor to outwardly expand for securing said anchor to said acetabular shell,
wherein said elongate anchor includes a concave proximal end that abuts said convex outer surface of said acetabular shell.

2. The implant assembly of claim 1, wherein said anchor includes a distal end, a proximal end, and a groove extending from said proximal end toward said distal end, wherein said groove accommodates outward expansion of said anchor.

3. The implant assembly of claim 1, wherein said anchor includes a distal end and a proximal end, said distal end of said anchor having an indentation formed therein, whereby said indentation is dimensioned to matingly engage a corresponding instrument.

4. The implant assembly of claim 1, wherein said bore in said anchor includes a first portion having a first diameter and a second portion having a second diameter, said second diameter being smaller than said first diameter, whereby a shoulder is defined between said first portion and said second portion.

5. The implant assembly of claim 1, wherein said anchor further includes a rib extending from an exterior surface of said anchor.

6. The implant assembly of claim 1, wherein said anchor further includes a thread extending from an exterior surface of said anchor.

7. The implant assembly of claim 1, wherein said acetabular shell and said elongate anchor are formed as separate, discrete components.

8. The implant assembly of claim 1 further comprising a fastener that is received through the aperture in said acetabular shell and within the bore formed in said anchor while said concave proximal end of said anchor abuts said convex outer surface of said acetabular shell.

9. The implant assembly of claim 1 further comprising a fastener dimensioned for receipt through said aperture in said acetabular shell and within said bore formed in said anchor, said fastener receivable in said bore so as to cause at least a portion of said anchor to outwardly expand for securing said anchor to said acetabular shell, wherein a wall of said bore is provided by said highly porous biomaterial such that receipt of said fastener within said bore places the fastener in contact with said highly porous biomaterial.

10. An implant assembly, comprising:
an acetabular shell formed from a biocompatible material, said acetabular shell having a polar axis, a concave inner surface, a convex outer surface, and an aperture extending through said acetabular shell from said concave inner surface to said convex outer surface, said aperture being non-coincident with said polar axis of said acetabular shell;
an anchor formed entirely from a highly porous biomaterial, said anchor having a bore formed therein; and
a fastener dimensioned for receipt through said aperture in said acetabular shell and within said bore formed in said anchor, wherein said fastener is receivable within said bore so as to cause at least a portion of said anchor to outwardly expand for securing said anchor to said acetabular shell.

11. The implant assembly of claim 10, wherein said anchor includes a distal end, a proximal end, and a groove extending from said proximal end toward said distal end, wherein said groove accommodates outward expansion of said anchor.

12. The implant assembly of claim 10, wherein said fastener is dimensioned to extend entirely through said bore formed in said anchor.

13. The implant assembly of claim 10, wherein said fastener is dimensioned to extend only partially through said bore formed in said anchor.

14. The implant assembly of claim 10, wherein said acetabular shell and said anchor are formed as separate, discrete components.

15. The implant assembly of claim 10, wherein said fastener has sufficient length to cause outward expansion of said anchor into a patient's surrounding bone.

16. The implant assembly of claim 10, wherein said highly porous biomaterial is a porous metal material.

17. The implant assembly of claim 10, wherein said highly porous biomaterial has a porosity of between 55 and 90 percent.

18. An implant assembly, comprising:
an acetabular shell formed from a biocompatible material, said acetabular shell having a polar axis, a concave inner surface, a convex outer surface, and an aperture extending through said acetabular shell from said concave inner surface to said convex outer surface, said aperture being non-coincident with said polar axis of said acetabular shell;
an elongate anchor formed at least in part of a highly porous biomaterial, said highly porous biomaterial having a porosity of between 55 and 90 percent, said anchor configured for securement to said acetabular shell, said anchor having a bore extending at least partially therethrough, said bore alignable with said aperture of said acetabular shell; and
a fastener dimensioned for receipt through said aperture in said acetabular shell and within said bore formed in said anchor, wherein said fastener is receivable within said bore so as to cause at least a portion of said anchor to outwardly expand for securing said anchor to said acetabular shell, wherein said fastener has sufficient length to extend within said bore of said anchor to a location beyond said convex outer surface of said acetabular shell, wherein said fastener is receivable within said bore of said anchor so as to cause outward expansion of said anchor at the location beyond said convex outer surface of said acetabular shell.

19. The implant assembly of claim 18, wherein said elongate anchor includes a first end located proximate said acetabular shell and an opposing second end that extends away from said acetabular shell, said portion of said anchor that expands outwardly being located at said first end proximate said acetabular shell.

20. An implant assembly, comprising:
an acetabular shell formed from a biocompatible material, said acetabular shell having a polar axis, a concave inner surface, a convex outer surface, and an aperture extending through said acetabular shell from said concave inner surface to said convex outer surface, said aperture being non-coincident with said polar axis of said acetabular shell; and
an elongate anchor formed entirely from a highly porous biomaterial, said highly porous biomaterial having a porosity of between 55 and 90 percent, said anchor configured for securement to said acetabular shell, said anchor having a bore extending at least partially therethrough, said bore configured to be aligned with said aperture of said acetabular shell so that a fastener can be received through said aperture in said acetabular shell and into said bore of said anchor to cause at least a portion of said anchor to outwardly expand for securing said anchor to said acetabular shell,
wherein said anchor is sized larger than said aperture in said acetabular shell such that, when said anchor is coupled to said acetabular shell, said anchor is positioned completely outside of said aperture in said acetabular shell.

21. An implant assembly, comprising:
an acetabular shell formed from a biocompatible material, said acetabular shell having a polar axis, a concave inner surface, a convex outer surface, and an aperture extending through said acetabular shell from said concave inner surface to said convex outer surface, said aperture being non-coincident with said polar axis of said acetabular shell;
an anchor formed entirely from a highly porous biomaterial, said anchor having a bore formed therein; and
a fastener dimensioned for receipt through said aperture in said acetabular shell and within said bore formed in said anchor, wherein said fastener is receivable within said bore so as to cause at least a portion of said anchor to outwardly expand for securing said anchor to said acetabular shell, wherein said fastener has sufficient length to extend within said bore of said anchor to a location beyond said convex outer surface of said acetabular shell, wherein said fastener is receivable within said bore of said anchor so as to cause outward expansion of said anchor at the location beyond said convex outer surface of said acetabular shell.

* * * * *